United States Patent [19]
Shine et al.

[11] Patent Number: 5,766,637
[45] Date of Patent: Jun. 16, 1998

[54] MICROENCAPSULATION PROCESS USING SUPERCRITICAL FLUIDS

[75] Inventors: Annette Dudok Shine, Newark, Del.; Jack Gelb, Jr., Landenberg, Pa.

[73] Assignee: University of Delaware, Newark, Del.

[21] Appl. No.: 727,154

[22] Filed: Oct. 8, 1996

[51] Int. Cl.$^6$ .............................. A61K 9/58; B01J 3/00; B01J 13/04
[52] U.S. Cl. .................... 424/497; 424/489; 428/402.22; 428/402.24; 264/4; 427/2.14; 427/212; 523/347; 106/23 C; 512/4
[58] Field of Search .................... 424/451, 489–495, 424/497; 428/402–402.24; 264/4, 5; 427/2.14, 212

[56] References Cited

U.S. PATENT DOCUMENTS

| | | | |
|---|---|---|---|
| 4,582,731 | 4/1986 | Smith | 427/421 |
| 4,734,451 | 3/1988 | Smith | 524/493 |
| 5,043,280 | 8/1991 | Fischer et al. | 424/489 |
| 5,271,881 | 12/1993 | Redding, Jr. | 264/432 |
| 5,424,076 | 6/1995 | Gorissen et al. | 424/501 |
| 5,508,060 | 4/1996 | Perman et al. | 427/2.14 |

OTHER PUBLICATIONS

Debenedetti et al., "Application of supercritical fluids for the production of sustained delivery devices", *J. Controlled Release*, 24:27–44 (1993).

Shine, "Polymers and Supercritical Fluids", *Physical Properties of Polymers Handbook*, Chapter 18, pp. 249–256, (James E. Mark ed. 1993).

Berens et al., "Application of Compressed Carbon Dioxide in the Incorporation of Additives into Polymers", *J. Applied Polymer Sci.*, vol. 16, pp. 231–242 (1992).

Eckert et al., "Supercritical fluids as solvents for chemical and materials processing", *Nature*, vol. 383, pp. 313–318, Sep. 26, 1996.

*Primary Examiner*—Edward J. Webman
*Attorney, Agent, or Firm*—Lerner, David, Littenberg, Krumholz & Mentlik

[57] ABSTRACT

The present invention comprises a method for microencapsulating a core material comprising the steps of a) mixing a core material with an encapsulating polymer, b) supplying a supercritical fluid capable of swelling the polymer to the mixture under a temperature and a pressure sufficient to maintain the fluid in a supercritical state, c) allowing the supercritical fluid to penetrate and liquefy the polymer while maintaining temperature and pressure sufficient to maintain the fluid in a supercritical state, and d) rapidly releasing the pressure to solidify the polymer around the core material to form a microcapsule. This method requires neither that the polymer nor core materials to be soluble in the supercritical fluid and can be used to rapidly and efficiently microencapsulate a variety of materials for a variety of applications.

54 Claims, 2 Drawing Sheets

MICROENCAPSULATION PROCESS USING SUPERCRITICAL FLUIDS

BACKGROUND OF THE INVENTION

1. Technical Field

The present invention relates to a method for microencapsulating materials, particularly temperature-labile or solvent-labile materials, in a polymeric substance. The present invention further relates to microencapsulated substances produced by these methods.

2. Description of the Background Art

Microencapsulation is a process whereby very small particles or droplets of an active or useful substance ("core") are coated with or embedded in a polymer ("shell"), which is essentially inert and serves a protecting or isolating function. The core material is released from the microcapsule through erosion, permeation or rupture of the shell. Microcapsules are useful in numerous applications, including protection or isolation of the core from the environment and the sustained or timed release of the core material. They are particularly useful in medical, pharmaceutical or veterinary formulations. Variation in the thickness or material of the shell can be utilized to control the rate or timing with which the core material is released from the microcapsule.

In order to form microcapsules, such as for controlled release applications, the encapsulating polymer must be processed in the fluid state. The prior art teaches three ways (with multiple variations) of doing this: (1) polymerize liquid monomers or prepolymers in the presence of the core material in order to form a shell around the core; (2) melt the polymer by raising its temperature; (3) dissolve the polymer in a solvent or solvents. The polymerization option (1) is highly chemistry-specific and requires that reactants and reaction conditions do not harm the core material. The melting option (2) requires polymers that melt at low enough temperatures so as to be harmless to the core material. This is often difficult to achieve in practice, particularly in medical and veterinary applications, where core materials are frequently temperature-labile and where microcapsules must have a sufficiently high melting temperature that they do not fuse together under storage conditions. Some version of the dissolution option (3) is the method most frequently used. In many cases, water is one of the solvents of choice. However, therapeutic agents tend to be soluble in water, and when microencapsulated therapeutic agents are needed to be released over or after a prolonged period of time, e.g., over weeks, it is often necessary for the encapsulating polymer to be insoluble in water. Otherwise, the microcapsule would dissolve in vivo before the target release time. Water-insoluble aliphatic polyesters, especially copolymers of lactic and glycolic acid (PLGA) which are used commercially as bioabsorbable surgical sutures, are very well-studied as controlled release polymers. These polymers are soluble in only a few organic solvents (e.g., ethyl acetate, methylene chloride, chloroform, dimethyl formamide, tetrahydrofuran and hexafluoroisopropanol). Furthermore, since their glass transition temperatures are about 50° C., melt processing of PLGA for microencapsulation is not feasible with many temperature-labile therapeutic agents. Consequently, when PLGA is used to microencapsulate a water-soluble therapeutic agent, the method of choice is usually a technique called the double emulsion method (also called the complex emulsion method).

In the double emulsion method, an aqueous solution of the therapeutic agent is emulsified with a larger quantity of non-aqueous solution of PLGA; the solvent is usually methylene chloride. This emulsion is then further emulsified in a still larger quantity of surfactant-containing water, forming a (water-in-oil)-in-water double emulsion. The polymer solvent ("oil") is then allowed to slowly evaporate, hardening the polymer and encapsulating the inner water droplets which contain the therapeutic agent. The double emulsion method can be useful for a wide variety of therapeutic agents, because the agent experiences only mild temperatures (frequently room temperature), and it has exposure to the solvent only at the inner water-oil interface.

The double emulsion method, however, has many drawbacks. The process is extremely long (at least 4 hours), is difficult to scale up, requires large volumes of solvent (about 15 grams solvent per gram polymer) and even more water (about 25 grams of water per gram of polymer), which results in large waste streams. In part because of the large volume of waste solvent, generally less than 85% of the therapeutic agent is actually encapsulated in the solid polymer. Furthermore, methylene chloride has been identified as a carcinogen, so its use is falling out of favor, both because of concerns over residual methylene chloride contamination in the microcapsules and because of strict environmental standards for its use.

Some groups have experimented with the use of supercritical or near-supercritical fluids as solvents in microencapsulation processes. A supercritical fluid ("SCF") is a dense gas that is maintained above its critical pressure and above its critical temperature (the temperature above which it cannot be liquefied by any amount of pressure). Though supercritical fluids have gas-like properties, such as high compressibility and low viscosity, they exhibit many of the properties of liquids, such as high density and high solvating power. A near-supercritical fluid is a fluid that is not technically supercritical, but displays many of the properties of a supercritical fluid, such as high solvating power and compressibility. The use of the term "supercritical fluid" in this specification is intended to encompass near-supercritical fluids. Even substances that are normally solids or liquids at room temperatures can be brought to a supercritical fluid state by the application of appropriate temperature and pressure. A detailed discussion of supercritical fluids and their properties can be found in Debenedetti et al., *J. Controlled Release* 24:27–44 at 28–29 (1993), Smith, U.S. Pat. No. 4,482,731 (col. 4 line 48 to col. 7 line 23) and in Shine, Chapter 18: Polymers and Supercritical Fluids in *Physical Properties of Polymers Handbook* 249–256, passim (James E. Mark ed. 1993), all hereby incorporated by reference.

It has been found that the rapid expansion of supercritical fluids causes precipitation of solutes dissolved therein, while the supercritical fluid solvent simply evaporates. Smith, U.S. Pat. Nos. 4,582,731 and 4,734,451. This phenomenon has been adapted for use in making pharmaceutical formulations of drug-loaded microparticles. Debenedetti, et al., supra. Debenedetti, et al. dissolved L-polylactic acid (L-PLA) and the drug lovastatin in supercritical $CO_2$, then released the solution through a nozzle, causing formation of microparticles. The rapid decrease in pressure resulted in co-precipitation of the polymer and drug into a heterogenous population of microparticles consisting of microspheres containing single lovastatin needles, larger spheres containing several needles, microspheres without protruding needles and needles without any polymer coating. Manipulation of temperature and pressure conditions permitted production of a fibrous network of needles connected by polymer. This process requires that both the core material and the shell material be soluble in the same supercritical fluid at the same temperature and pressure. Furthermore, variability in the relative rates of precipitation of the two materials results in a heterogenous population of microspheres, as can be seen in part from the results of the Debenedetti group.

Another microencapsulation process involving an "abrupt pressure change," although without the use of supercritical fluids, is discussed in Redding, Jr., U.S. Pat. No. 5,271,881. This process involves using cycles of high and low pressure, brought about by a piston or by ultrasonic waves, to precipitate shell material around a dispersed core material. As noted, this process does not involve the use of supercritical fluids but rather relies on unspecified physical forces, possibly cavitation or shear forces, to cause precipitation of the shell material. The liquid dispersion of core and shell material must be virtually incompressible in order for the forces to have effect. Using this process, it is asserted to be possible to precipitate multiple shells about a core, using a multi-staged process.

Although each of these methods can be useful, there remains a need in the art for a rapid, efficient microencapsulation method that does not require the use of organic solvents or high temperatures that might adversely affect the environment or the microencapsulated material.

SUMMARY OF THE INVENTION

The present invention comprises a method for microencapsulating a core material comprising the steps of a) mixing a core material with a microencapsulating polymer in either a solid particulate or liquid form, b) supplying to the mixture a supercritical fluid capable of dissolving in the polymer under a pressure and temperature sufficient to maintain the fluid in a supercritical state, c) allowing the supercritical fluid to penetrate and swell or liquefy the polymer while maintaining pressure and temperature sufficient to maintain the fluid in a supercritical state, and d) rapidly releasing the pressure to solidify the polymer around the core material to form a microcapsule. This method requires neither the core materials nor the polymer to be soluble in the supercritical fluid; it requires only that the supercritical fluid be soluble in the polymer.

This method avoids the use of the organic solvents used in some traditional microencapsulation processes, not only eliminating any problems associated with the presence of residual solvent in the microcapsules or waste stream, but also permitting microencapsulation of materials incompatible with traditional processes due to their sensitivity to the presence of organic solvents. Furthermore, the ability of the process to function at relatively low temperatures as compared to the normal melting or glass transition point of the shell material permits microencapsulation of temperature-labile substances that otherwise would be degraded or inactivated at the temperatures required by those traditional processes that call for melting the shell material.

DETAILED DESCRIPTION

The present invention relates to methods for microencapsulating active ingredients under relatively mild conditions by polymer liquefaction using supercritical solvation (PLUSS). A supercritical fluid is used to swell or liquefy a polymeric substance at temperatures significantly below the melting point (for crystalline polymers) or the glass transition point (for amorphous polymers) of the polymer. Intimate mixture under pressure of the polymer material with a core material, either before or after supercritical fluid salvation of the polymer, followed by an abrupt release of pressure, leads to an efficient solidification of the polymeric material around the core material. This method is particularly useful for microencapsulating core material that would be adversely affected by the temperatures required to melt polymeric shell materials under normal atmospheric conditions or that would be adversely affected by the presence of the organic solvents typically used to dissolve polymeric materials in traditional microencapsulation methods.

As used herein the term "microcapsule" encompasses both a particle comprising a monolithic core surrounded by polymer and a particle comprising a dispersion of core material in a polymer matrix.

As used herein the term "shell material" refers to the material that forms the outer coating or the matrix of the microcapsule. Though the shell is generally inert in the application in which the microcapsule is used, and serves the function of isolating, protecting or controlling the release of the core material from the microcapsule into the environment, the shell material may have some functionality, such as biochemical attractant moieties or ionic functionalities. The release of the core material from the shell is generally achieved by erosion, permeation, chemical degradation or rupture of the shell.

As used herein the term "core material" refers to the material inside and surrounded by the shell of the microcapsule. The "core" can be either a single particle or droplet surrounded by a layer of shell material, or a dispersion of particles or droplets in a matrix of shell material. It is the core material that is the primary active agent in the application in which the microcapsule is used, be it the dye compound in a dye composition or the drug in a pharmaceutical composition. Core material can be a crystalline or amorphous solid, or a liquid, solution or suspension. As the goal in a microencapsulation process is to achieve small particles of the core material surrounded by or embedded in a shell, the core material should be finely dispersible form, be it solid or fluid.

Many substances that are used as core materials are temperature-labile or organic solvent-labile. By "temperature-labile" it is meant that the properties of the core material are adversely affected by temperatures above a certain upper temperature limit, above which the physical properties, function or activity of the core material is adversely affected. Examples of adverse effects caused by elevated temperatures on temperature-labile core materials are chemical break-down, loss of biological activity and polymerization. By "organic solvent-labile" it is meant that the properties of the core material are adversely affected by the presence of an organic solvent (such as acetone, toluene, xylene, methylene chloride, ethanol, etc.). Adverse effects include chemical change or re-arrangement, loss of biological activity and dehydration.

As used herein the term "supercritical fluid" ("SCF") should be considered to encompass near-supercritical fluids (highly compressed fluids that are below the critical temperature point, yet exhibit many of the same qualities of true supercritical fluids, such as high solvating power and compressibility). Likewise a "supercritical state" should be considered to encompass a near-supercritical state. Supercritical fluids can be combinations of substances, such as $CO_2$ with $CHClF_2$.

Preferably, the polymeric shell material and the core material are thoroughly mixed while the polymer is in a solid particulate form prior to the introduction of a supercritical fluid solvent into the system. The polymer and core material preferably are further mixed after polymer liquefaction to achieve an intimate mixture of liquefied polymer and core particles or droplets. If the core material is a liquid (meaning it is a substance in a fluid form or a solution or suspension of a solid), an emulsion should be formed of the core material in the liquefied polymer. Heat can be added to or removed from the system at any time to aid solvation of the polymer. In some situations it may be necessary to liquefy the polymer before addition of the core material. For instance, in applications where the core material is temperature-labile and the temperature required to liquefy the polymer in the supercritical fluid exceeds the upper temperature limit below which the core material is stable, it may be necessary to first liquefy the polymer at the higher temperature, then supercool the liquid to a temperature tolerated by the core material, add the core material and mix.

This process can be applied to a wide variety of core materials such as dyes, inks, adhesives, scents, deodorants, disinfectants, herbicides, pesticides, fungicides, fertilizers, food flavorings and food colorants. Sensitivity to the temperatures and pressures necessary for maintaining supercritical conditions is the only practical limitation on core material selection. The process has particular utility for the microencapsulation of medical, pharmaceutical and veterinary compositions of bioactive agents such as antibiotics, nutritional supplements (such as vitamins and minerals), metabolism modifiers (such as hormones and appetite suppressants), therapeutic agents, analgesics and vaccines. The medical, pharmaceutical or veterinary application of this process is particularly useful for those agents which are temperature-labile or organic solvent-labile, and/or which are desired to be released into the body in a timed or sustained manner, or isolated or protected from the environment for ease of handling and/or ease and stability of storage. An example of such agents are live vaccines comprising lipid-enveloped virus. Such a live vaccine is both temperature-labile and organic solvent-labile because the vaccine loses its effectiveness when exposed to high temperatures and to organic solvents—elevated temperatures will kill the virus and cause degradation or denaturation of the nucleic acid and coat proteins that are its constituents, and an organic solvent would strip away the lipid envelope, also killing the virus. Further, microencapsulation of a live virus serves the function of isolating it from the environment, including the internal environment of the animal to which it is administered, until administered or released, permitting not only safe storage and handling of the vaccine, but also thereby avoiding premature exposure of the vaccine to the animal that could lead to its inactivation (e.g., Infectious Bursal Disease Virus vaccine, administered to chickens, can be inactivated by maternal antibodies in young chicks—microencapsulation protects the vaccine until the levels of these antibodies decline naturally).

Microencapsulation using the methods of the present invention can be achieved at a variety of polymer-to-core material ratios, however, below ratios of about 1:1 there is insufficient shell material to completely surround the core material. At high polymer-to-core ratios, the overall concentration of core material in the microcapsule could become too low to be useful (for example, with Infectious Bursal Disease Virus vaccine, already greater than 99% inert material, above ratios of about 20:1 there is too little active material to be effective at a practical dose volume; however, higher ratios can be used if a highly purified vaccine is used). There is, however, no known inherent upper limit. Additives, such as water, also can be included in the system and can, for instance, aid salvation or emulsion.

A preferred embodiment of the present invention is the use of PLUSS to microencapsulate live virus vaccines such as Infectious Bursal Disease Virus vaccine or vaccines containing live enveloped virus (virus surrounded by a lipid layer). In this preferred embodiment a bioerodible polymer (such as polycaprolactone or poly lactic/glycolic acid copolymer) in a fine powder form is mixed with a dry vaccine preparation likewise in fine powder form. Suitable polymer:vaccine ratios for this preferred embodiment are from about 2:1 to about 10:1, preferably about 5:1. The mixed polymer/vaccine powder is charged to a pressure vessel where a supercritical fluid is added, preferably supercritical $CO_2$ (though other SCFs such as supercritical $N_2O$ also are suitable). The $CO_2$ also can be supplied in a non-supercritical state, then be brought to a supercritical state. This preferred embodiment also will operate with $CO_2$ at near-supercritical conditions (e.g., at 21° C. instead of the critical temperature of 31° C.). Supercritical $CO_2$ can be supplied in ratios of about 0.05 gram $CO_2$ per gram polymer to about 4 grams $CO_2$ per gram polymer. A preferred solvent:polymer ratio is about 2 grams solvent per gram polymer. Pressure is preferably maintained between about 1000 and 6000 psi, preferably 4000 psi, to maintain the supercritical state of the fluid while the polymer is liquefied by the supercritical fluid. After liquefaction is complete, pressure is released rapidly, permitting the polymer to expand and the SCF to evaporate, forming microcapsules of polymer-enclosed core material. A typical batch processing time in this preferred embodiment is about 2 hours, most of which is devoted to the polymer liquefaction step. Once liquefaction or swelling of the polymer has occurred, and intimate mixture with the core material is established, the process can move directly to the depressurization step.

Any polymer that is subject to swelling by a supercritical fluid and that is compatible with the desired application can be used in the present invention. Swelling is a process whereby the supercritical fluid dissolves in or permeates the polymer, leading to a depression of the polymer's melting point. This depression of the polymer's melting-point allows it to liquefy (i.e. become fluid without dissolving) at sub-melting-point temperatures. In an SCF-swelled polymer, the SCF is a minor component in the system, unlike dissolution, where it is a major component in the system. Although any SCF that dissolves a polymer can swell it, not every SCF that swells a polymer will dissolve it. Shine, *Polymers and Supercritical Fluids*, incorporated by reference supra, lists numerous polymers which dissolve in supercritical fluids, and hence also swell in those supercritical fluids, along with supercritical fluids in which the polymers are soluble (see, e.g., Shine Table 18.3). This reference also lists the temperature and pressure parameters within which supercritical fluid dissolution occurs for these SCF/polymer combinations. This reference also lists polymers which are known to swell and liquefy in the presence of carbon dioxide specifically (see, e.g., Shine Table 18.4). Persons of ordinary skill in the art can use references such as this to assist in selecting polymers and SCFs for use in the present invention. Although the higher molecular weight polymers can be more difficult to work with (e.g. they tend to plug up the lines), there are no process limitations on the types of polymers that can be used. Several polymers which are used in medical and pharmaceutical formulation applications can be swelled by supercritical fluids, including polymethyl acrylate, polycaprolactone, poly-L-lactic acid, poly DL-lactic acid, polyglycolic acid and polylactic/glycolic acid copolymer. Several of these polymers are soluble in supercritical fluids which are relatively inert and nontoxic, such as carbon dioxide. A partial list of polymers useful in medical, pharmaceutical and veterinary applications includes the following:

poly(glycolic acid)
  poly(lactic acid)
  poly(caprolactone)
  poly(hydroxy butyric acid)
  poly(hydroxy valeric acid)
  poly(ethylene adipate)
  co- or terpolymers of the above, especially lactic/glycolic and butyric/valeric co- or terpolymers
  poly (ortho esters)
  poly (anhydrides)
  poly (1,4-dioxane-2,5-diones)
  polyoxylates
  poly (1,3-dioxane-2-one) and its copolymers
  poly (p-dioxanone)
  poly (amino acids)
  pseudopoly (amino acids)
  poly (amides) (e.g., gelatin)
  cellulosics (e.g., cellulose, cellulose acetate butyrate, carboxyl methyl cellulose, hydroxy propyl cellulose).

Selection of an appropriate polymer for use in a particular application would be governed largely by the application contemplated. For instance, in medical and veterinary applications, biocompatible, non-water-soluble, bioerodible or permeable polymers that do not break down into toxic degradation products are most suitable. Generally, polymers useful for medical, pharmaceutical or veterinary applications will be biodegradable or hydrolyzable and will contain a carbonyl or ether (including cyclic ether) linkage. For non-medical or non-veterinary uses, virtually any polymer which can be swelled by a supercritical fluid can be used, as long as the polymer and supercritical fluid are compatible with the core material to be encapsulated, a determination which is readily made from information available in the published literature. All varieties of copolymers of preferred polymers can be used.

Selection of the supercritical fluid is largely determined as a function of the selection of the polymer, the selection of the two being made together to suit the needs of the user. Considerations of toxicity and general ease of handling of the SCF is a principal consideration. The fluid also must swell the polymer to a sufficient extent so that, when the pressure on the mixture is released, the fluid will occupy the overwhelming majority (e.g. >90%, preferably >95%, and most preferably >99%) of the total volume of the mixture. Practically speaking, this requires that the fluid have an appropriate combination of high density (i.e., much greater than the density at atmospheric temperature and pressure) and high solubility in the polymer. Typically, both density and solubility increase with increasing pressure, but solubility may either increase or decrease with increasing temperature, depending on the polymer/fluid mixture. High solubility and high density are features of supercritical fluids that are also found in compressed liquids, so compressed liquids may also be suitable for the process.

Depending on which process constraints are paramount—the need for a particular shell property, limitations on solvating conditions such as temperature and pressure, or concern over the presence of toxins in the waste stream or as a residue in the final product—the selection will be governed more by SCF properties or by polymer properties. On the whole, selection of an appropriate polymer/SCF combination suited for a particular application is within the ordinary skill in the art. It should be noted that the nature of the core material per se actually imposes few practical restrictions on the choice of the polymer/SCF combination, apart from situations where an organic compound (such as ethane, propane or $CHClF_2$) is used as the supercritical fluid and the core material is adversely affected by the presence of that organic compound. Therefore, a particular polymer/SCF combination can be used under virtually identical process parameters (pressure, temperature, polymer/core and polymer/SCF ratios) for a variety of core materials.

Figure 1:
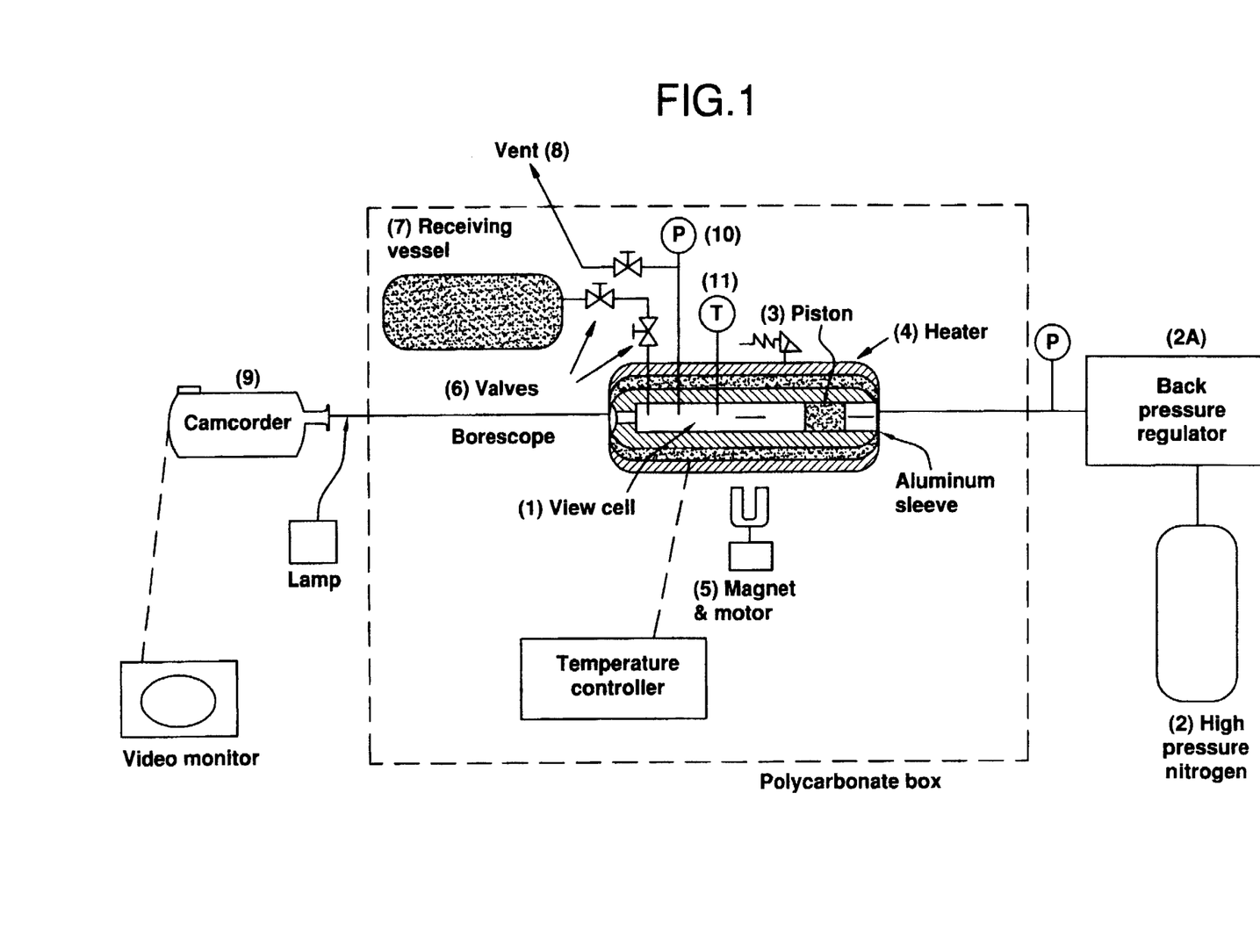
FIG. 1 represents one apparatus useful for forming microparticles by polymer liquefaction using supercritical salvation.

FIG. 1 is a schematic diagram of an apparatus useful in performing a preferred embodiment of the process of the present invention wherein the supercritical fluid is a gas at room temperature. Polymeric coating material is introduced into the view cell 1 which is connected to a supply of the SCF swelling material (not shown), and through a back-pressure regulator 2A to a source of high pressure fluid 2, such as nitrogen, water or hydraulic fluid. The view cell comprises a piston 3 which is moved by the application of the high pressure inert gas. The apparatus optionally can have a heater 4 for the application of heat should that be necessary to fully liquefy the polymer. The core substance is charged to the view cell either before or after polymer liquefaction, the polymer and core material being intimately mixed by means of a magnetic stirring rod moved by a magnetic motor 5. Once intimate mixture is achieved between the liquefied polymer and the core material, valves 6 are opened permitting expansion of the polymer/core material mixture into a receiving vessel 7. The supercritical fluid returns to a gaseous state during this process and escapes through a vent 8. A camcorder or other viewing or recording device 9 may be attached to the view cell in such a manner to permit observation of the mixing and expansion processes. Similarly, pressure probes 10 and temperature probes 11 can be incorporated to permit monitoring of these parameters during the process.

Figure 2:
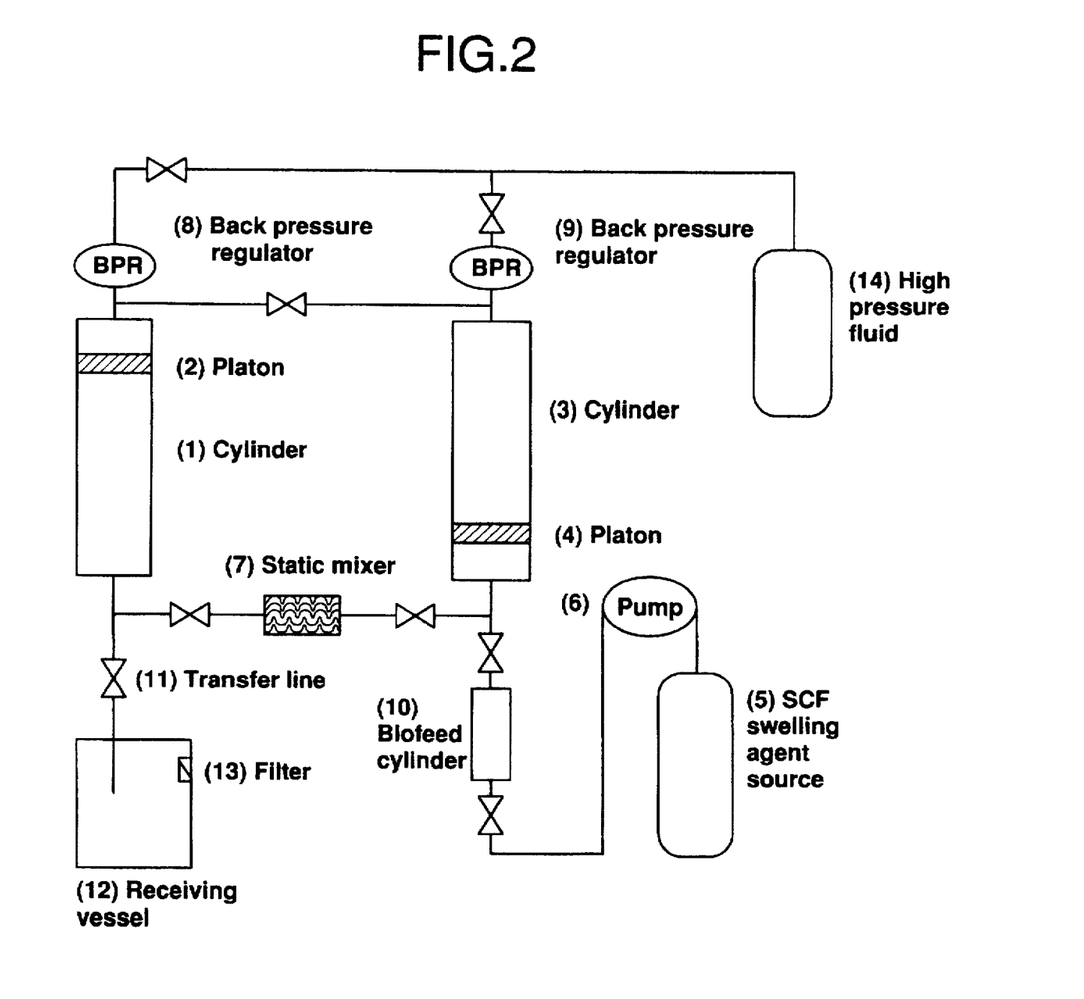
FIG. 2 represents a second apparatus useful for forming microparticles by polymer liquefaction using supercritical salvation.

FIG. 2 is a schematic diagram of another apparatus useful in performing a preferred embodiment of the process of the present invention. Polymeric coating material is introduced into cylinder 1 with piston 2 partially advanced and piston 4 fully advanced in cylinder 3. The supercritical fluid swelling agent 5 is added by pump 6 to cylinder 1, passing through static mixer 7. Desired pressure is applied to cylinder 1 by adjusting back pressure regulator 8, which is connected to a source of high pressure fluid, 14. The polymer can be allowed to soak in the swelling agent in cylinder 1 in order to facilitate liquefaction. The core material to be encapsulated is placed in the biofeed cylinder 10, which is pressurized with the SCF swelling agent 5, forcing the core material into cylinder 3. The polymer, core material and SCF swelling agent then are thoroughly mixed by repeated passing through static mixer 7, due to the reciprocating action of pistons 2 and 4, which are controlled by back pressure regulators 8 and 9. The temperature in the cylinders 1 and 3 and static mixer 7 is controlled by a surrounding air bath (not shown). In this apparatus, it is possible initially to liquefy the polymer with SCF swelling agent at a somewhat elevated temperature, and subsequently lower the temperature before mixing in the core material, in order to minimize exposure of the core to prolonged elevated temperature. After all components have been thoroughly mixed, the mixture is forced into transfer line 11, which may optionally have a nozzle at its end, into receiving vessel 12, which is maintained at a pressure, usually atmospheric, which is much lower than the pressure in the cylinders. The SCF swelling agent, now a gas, is vented through filter 13, while the polymer-encapsulated core material remains in receiving vessel 12.

Any suitable apparatus which permits intimate mixture of the polymer and core materials, the introduction of the supercritical fluid at a pressure sufficient to maintain its supercritical state, release of pressure from the system, expansion of the preparation and separation of the SCF can be used for this process. The selection and/or manufacture of such apparatus is within the ordinary skill in the art and can be done using components which are easily constructed or obtained from commercial suppliers.

The process of the present invention results in a product having core material efficiently encapsulated by polymeric material, resulting in little waste of ingredients. The encapsulated material can be recovered either as fine particles, elongated particles, or a highly porous structure which can be easily ground into particles of the desired size range. This is highly desirable as the substances used as core materials are frequently expensive and/or difficult to manufacture. The encapsulated product is readily processed by per se known methods into any number of suitable forms, such as free-flowing powders, suspensions, coatings or tablets. For instance, microcapsules could be compressed with excipients into tablets, or mixed in a buffered aqueous solution to form an injectable formulation, or applied as a slurry and dried as a surface coating. The nature of the secondary processing is governed by the ultimate use to which the product will be put, and these secondary processing methods are per se known in the art.

The following examples, in the veterinary art, are meant to illustrate but in no way to limit the present invention. The broad applicability of this process to numerous technical fields is apparent and persons of ordinary skill in numerous technical fields will be able to adapt this process and the products made thereby in a variety of ways within the scope of the claimed invention.

EXAMPLE 1

Polycaprolactone (PCL) (mol. wt. 4000) was ground to a powder with a mortar and pestle and then refrigerated. The contents of two vials of Infectious Bursal Disease Virus (IBDV) vaccine (Serial No. 2491) were ground in a mortar and pestle. The ground IBDV vaccine was weighed at 0.9803 g then placed in a sterile bag and refrigerated. The PCL and vaccine were mixed in a 5:1 ratio (4.9042 g PCL to 0.9803 g vaccine) in the sterile bag and shaken until they appeared uniformly dispersed. The mixture then was charged to the view cell of the PLUSS apparatus (see FIG. 1).

After charging, the cell was sealed and $CO_2$ was charged to a pressure of 4,000 PSI. The polymer/vaccine/$CO_2$ mixture was soaked for two hours at 22° C. and 4,000 PSI, after which the temperature was gradually raised to 37.5° C. Initial polymer liquefaction was observed at approximately 26.5° C.; liquefaction was complete at 37.5° C. Only one polymer rich phase was apparent. No $CO_2$ rich phase was visible, apart from bubbles at the top of the view cell. The IBDV vaccine appeared insoluble or incompletely miscible in the polymer/$CO_2$ phase with polymer and vaccine partitioned into white and orange areas, respectively.

Pressure was released by opening the valve to the polymer collection chamber. Expansion of the fluid polymer was sudden and complete. Approximately 84% of the charged solids were recovered from the collection chamber and view cell. The expanded solids removed were fine to porous. Under a light microscope the expanded solids appeared as agglomerations of fine particles. Large particles were easily separable into smaller particles by application of light pressure. Samples were frozen for later analysis.

EXAMPLE 2

Microencapsulated vaccine samples prepared according to Example 1 were thawed and assayed for IBDV viability. Samples were first washed 3 times with sterile water in order to remove any virus which was not encapsulated. After washing, the microcapsules were dissolved in methylene chloride to release the encapsulated virus. The IBDV was extracted from the methylene chloride solution by contacting it with sterile water. Both the water used to wash the encapsulated vaccine and the water extract from the methylene chloride solution were assayed for IBDV viability by a standard microtiter technique and compared with a control IBDV which was not subjected to PLUSS encapsulation. Briefly, the water solutions were further diluted ($1:10^1$–$1:10^6$) in sterile diluent. The dilutions were inoculated onto primary chicken embryos fibroblast (CEF) cells in 96-well microtiter plates and were incubated at 37° C. in a 5% $CO_2$ incubator. Titration endpoints were determined at the point where the CEFs exhibited cytopathic effects such as cell rounding and degeneration, generally 4–5 days after IBDV inoculation. IBDV titers were calculated by the method of Reed and Muench ("A simple method for estimating fifty percent endpoints," Am. J. Hyg. 27:439–497 (1938)). The results are set forth in Table I, below. Since infectivity assays are dependent on the ability of a virus to infect, replicate and damage cells such as CEFs, the assay results indicate the amount of live infectious virus associated with the surface and interior of the polymer microcapsules. The higher the titer values, the greater the concentration of live infectious virus. A difference in titer values of one unit corresponds to a factor of 10 difference in virus concentration.

TABLE I

| SAMPLE | TITER |
| --- | --- |
| Water from third washing (surface virus) | 4.2 |
| Water from methylene chloride extraction (encapsulated virus) | 5.7 |
| Control | 5.7 |

We claim:

1. A method for microencapsulating a core material comprising a. mixing a core material with a microencapsulating polymer, b. supplying to the mixture a supercritical fluid capable of swelling the polymer under a temperature and a pressure sufficient to maintain the fluid in a supercritical state, c. allowing the supercritical fluid to penetrate and liquefy the polymer, without dissolving the polymer, while maintaining temperature and pressure sufficient to maintain the fluid in a supercritical state, and d. rapidly releasing the pressure to solidify the polymer around the core material to form a microcapsule.

2. The method of claim 1 wherein the core material is an organic solvent-labile material.

3. The method of claim 1 wherein the core material is a temperature-labile material, and wherein liquefaction of the polymer occurs at a temperature below that at which the temperature-labile material is adversely affected.

4. The method of claim 1 wherein the core material comprises an herbicide, a pesticide, a fungicide or a fertilizer.

5. The method of claim 1 wherein the core material comprises a dye, an ink, an adhesive, a scent or a deodorant.

6. The method of claim 1 wherein the core material comprises a nutritional supplement, a metabolism modifier, an antibiotic, an analgesic, a therapeutic agent or a vaccine.

7. The method of claim 6 wherein the core material comprises a vaccine.

8. The method of claim 7 wherein the vaccine comprises a live virus.

9. The method of claim 7 wherein the core material comprises a subunit vaccine.

10. The method of claim 7 wherein the core unit comprises an inactivated vaccine.

11. The method of claim 7 wherein the core material comprises a recombinant vaccine.

12. The method of claim 7 wherein the vaccine comprises a non-enveloped virus.

13. The method of claim 12 wherein the live virus is Infectious Bursal Disease Virus.

14. The method of claim 7 wherein the vaccine comprises a virus having a lipid envelope.

15. The method of claim 1 wherein the polymer is a bioerodible polymer.

16. The method of claim 1 wherein the microencapsulating polymer is an aliphatic polyester.

17. The method of claim 15 wherein the aliphatic polyester is selected from the group consisting of polycaprolactone, poly(glycolic acid), poly(lactic acid), poly(hydroxy butyrate), poly(hydroxy valerate), poly(ethylene adipate), lactic/glycolic acid copolymers, hydroxybutyrate/hydroxyvalerate copolymers.

18. The method of claim 1 wherein the supercritical fluid comprises supercritical $N_2O$ or supercritical $CO_2$.

19. The method of claim 18 wherein the supercritical fluid is supercritical $CO_2$.

20. A method for microencapsulating temperature-labile core materials comprising
   a. mixing a microencapsulating polymer with a supercritical fluid capable of swelling the polymer, the mixing occurring at a temperature and a pressure sufficient to maintain the fluid in a supercritical state and at a temperature sufficient to liquefy the polymer, and whereby the polymer is liquefied but not dissolved,
   b. supercooling the liquefied polymer to a temperature below that which adversely affects the temperature-labile core material while maintaining a temperature and a pressure sufficient to maintain the supercritical fluid in a supercritical state,
   c. mixing the temperature-labile material with the supercooled liquefied polymer while maintaining a temperature and a pressure sufficient to maintain the supercritical fluid in a supercritical state,
   d. releasing the pressure to solidify the polymer around the temperature-labile material to form microcapsules.

21. The method of claim 20 wherein the core material is an organic solvent-labile material.

22. The method of claim 20 wherein the core material comprises an herbicide, a pesticide, a fungicide or a fertilizer.

23. The method of claim 20 wherein the core material comprises a dye, an ink, an adhesive, a scent or a deodorant.

24. The method of claim 20 wherein the core material comprises a nutritional supplement, a metabolism modifier, an antibiotic, an analgesic, a therapeutic agent or a vaccine.

25. The method of claim 24 wherein the core material comprises a vaccine.

26. The method of claim 25 wherein the vaccine comprises a live virus.

27. The method of claim 25 wherein the vaccine comprises a subunit vaccine.

28. The method of claim 25 wherein the vaccine comprises an inactivated vaccine.

29. The method of claim 25 wherein the vaccine comprises a recombinant vaccine.

30. The method of claim 25 wherein the vaccine comprises a non-enveloped virus.

31. The method of claim 30 wherein the live virus is Infectious Bursal Disease Virus.

32. The method of claim 25 wherein the vaccine comprises a virus having a lipid envelope.

33. The method of claim 20 wherein the polymer is a bioerodible polymer.

34. The method of claim 20 wherein the microencapsulating polymer is an aliphatic polyester.

35. The method of claim 34 wherein the aliphatic polyester is selected from the group consisting of polycaprolactone, poly(glycolic acid), poly(lactic acid), poly(hydroxy butyrate), poly(hydroxy valerate), poly (ethylene adipate), lactic/glycolic acid copolymers, hydroxybutyrate/hydroxyvalerate copolymers.

36. The method of claim 20 wherein the supercritical fluid comprises supercritical $N_2O$.

37. The method of claim 20 wherein the supercritical fluid comprises supercritical $CO_2$.

38. A method for microencapsulating a core material comprising
   a. mixing a core material with a microencapsulating polymer,
   b. supplying to the mixture a supercritical fluid capable of dissolving the polymer but incapable of dissolving the core material under a temperature and a pressure sufficient to maintain the fluid in a supercritical state,
   c. allowing the supercritical fluid to penetrate and dissolve the polymer while maintaining temperature and pressure sufficient to maintain the fluid in a supercritical state, and
   d. rapidly releasing the pressure to precipitate the polymer around the core material to form a microcapsule.

39. The method of claim 38 wherein the core material is a temperature-labile material, and wherein liquefaction of the polymer occurs at a temperature below that at which the temperature-labile material is adversely affected.

40. The method of claim 38 wherein the core material comprises an herbicide, a pesticide, a fungicide or a fertilizer.

41. The method of claim 38 wherein the core material comprises a dye, an ink, an adhesive, a scent or a deodorant.

42. The method of claim 38 wherein the core material comprises a nutritional supplement, a metabolism modifier, an antibiotic, an analgesic, a therapeutic agent or a vaccine.

43. The method of claim 42 wherein the core material comprises a vaccine.

44. The method of claim 38 wherein the polymer is selected from the group consisting of polycaprolactone, poly(glycolic acid), poly(lactic acid), poly(hydroxy butyrate), poly(hydroxy valerate), poly(ethylene adipate), lactic/glycolic acid copolymers, hydroxybutyrate/hydroxyvalerate copolymers.

45. The method of claim 38 wherein the supercritical fluid comprises supercritical $N_2O$ or supercritical $CO_2$.

46. A method for microencapsulating temperature-labile core materials comprising
   a. mixing a microencapsulating polymer with a supercritical fluid capable of dissolving the polymer but incapable of dissolving the core material, the mixing occurring at a temperature and a pressure sufficient to maintain the fluid in a supercritical state and at a temperature sufficient to liquefy the polymer, and whereby the polymer is liquefied,
   b. supercooling the liquified polymer to a temperature below that which adversely affects the temperature-labile core material while maintaining a temperature and a pressure sufficient to maintain the supercritical fluid in a supercritical state,
   c. mixing the temperature-labile material with the supercooled liquified polymer while maintaining a temperature and a pressure sufficient to maintain the supercritical fluid in a supercritical state,
   d. releasing the pressure to solidify the polymer around the temperature-labile material to form microcapsules.

47. The method of claim 46 wherein the core material comprises an herbicide, a pesticide, a fungicide or a fertilizer.

48. The method of claim 46 wherein the core material comprises a dye, an ink, an adhesive, a scent or a deodorant.

49. The method of claim 46 wherein the core material comprises a nutritional supplement, a metabolism modifier, an antibiotic, an analgesic, a therapeutic agent or a vaccine.

50. The method of claim 49 wherein the core material comprises a vaccine.

51. The method of claim 46 wherein the polymer is selected from the group consisting of polycaprolactone, poly(glycolic acid), poly(lactic acid), poly(hydroxy butyrate), poly(hydroxy valerate), poly(ethylene adipate), lactic/glycolic acid copolymers, hydroxybutyrate/hydroxyvalerate copolymers.

52. The method of claim 46 wherein the supercritical fluid comprises supercritical $N_2O$ or supercritical $CO_2$.

53. A method of claim 50 wherein the vaccine comprises a non-enveloped virus.

54. A method of microencapsulating Infectious Bursal Disease Virus vaccine comprising
   a. mixing Infectious Bursal Disease Virus vaccine in particulate form with polycaprolactone in particulate form,
   b. exposing the vaccine/polycaprolactone mixture to supercritical $CO_2$ at a temperature and a pressure sufficient to maintain the $CO_2$ in a supercritical state,
   c. allowing the supercritical $CO_2$ to penetrate and liquefy the polycaprolactone while maintaining a temperature and a pressure sufficient to maintain the $CO_2$ in a supercritical state,
   d. rapidly releasing the pressure to solidify the polycaprolactone around the Infectious Bursal Disease Virus vaccine particles to form a microcapsule.

* * * * *

UNITED STATES PATENT AND TRADEMARK OFFICE
CERTIFICATE OF CORRECTION

PATENT NO.    : 5,766,637
DATED         : June 16, 1998
INVENTOR(S)   : Shine et al.

It is certified that error appears in the above-identified patent and that said Letters Patent is hereby corrected as shown below:

Column 3, lines 59-60, delete "salvation" and insert therefor --solvation--.
Column 3, line 63, delete "salvation" and insert therefor --solvation--.
Column 4, lines 7-8, delete "salvation" and insert therefor --solvation--.
Column 6, line 7, delete "salvation" and insert therefor --solvation--.

Signed and Sealed this

Twenty-ninth Day of September, 1998

Attest:

BRUCE LEHMAN

*Attesting Officer*    *Commissioner of Patents and Trademarks*